United States Patent [19]

Mima et al.

[11] 3,945,889

[45] Mar. 23, 1976

[54] PREPARATION OF HUMAN PLACENTAL HYALURONIDASE

[75] Inventors: Yasuhiro Mima, Takatsuki; Masaaki Yamada, Kyoto, both of Japan

[73] Assignee: The Green Cross Corporation, Japan

[22] Filed: Aug. 27, 1974

[21] Appl. No.: 500,939

[30] Foreign Application Priority Data

Aug. 28, 1973  Japan................................ 48-97066

[52] U.S. Cl.................................. 195/62; 195/66 R
[51] Int. Cl.².......................................... C07G 7/026
[58] Field of Search............................ 195/66 R, 62

[56] References Cited
UNITED STATES PATENTS

2,808,362  10/1957  Thompson et al................ 195/66 R

OTHER PUBLICATIONS

Ponomareva–Chemical Abstract, Vol. 74, 84840n (1971) of Biol. Nauki 1970 (12), 25–6 (Russ.).

*Primary Examiner*—Lionel M. Shapiro
*Attorney, Agent, or Firm*—Cushman, Darby & Cushman

[57] ABSTRACT

Human placental hyaluronidase preparation is prepared by extracting hyaluronidase from human placenta with an aqueous alkaline solution, harvesting globulin fraction from the extract, selectively adsorbing hyaluronidase contained in the fraction on an anion exchanger such as DEAE-Cellulose and eluting it, gel-filtrating the eluate, and lyophilizing the filtrate into powder. The hyaluronidase thus obtained has a molecular weight of about 70,000, with isoelectric point of pH 5.2, and enzymatic optical pH ranging 3.6 – 4.0, differing from conventional bovin testicular hyaluronidase. The preparation contains no heterogeneous proteins which cause ill-effect to human body.

14 Claims, No Drawings

PREPARATION OF HUMAN PLACENTAL HYALURONIDASE

This invention relates to a human placental hyaluronidase preparation and process therefor.

The name, hyaluronidase, is commonly applied to a group of enzymes that are capable of hydrolyzing hyaluronic acid. This enzyme is widely distributed in nature, i.e., mammalian testis, liver and spleen, snake venoms, and certain bacteria. It has already been known that especially in mammalian testis, this enzyme has been found in relatively large amounts and usually animal testis is used as its source. Hyaluronidase itself has also been called as the "Spreading Factor" because of the property it has of enhancing the diffusion in tissues by modifying the permeability of tissue in vivo, and preparation of hyaluronidase obtained from the animal testis has widely been applied clinically in order to get better absorption of injected drugs. Nevertheless, hyaluronidase preparations obtained from such heterogeneous tissues as animal testis or bacteria, happen to induce critical ill-effects due to its heterogeneous protein when being injected into patients, and attention should be paid before and during its administration.

Little has been known on the presence of hyaluronidase in human placental tissue, and the physiological significance as well as clinical role of the enzyme has not yet been elucidated. [F. Scarpa, A. Panazzolo, M. Tanferna, and P. F. Pavetto: Boll. Soc. Ital. Biol. Sper. 45 217 – 220 (1969); I. P. Homenyuk: Pediatr. Akush. Hinekol. 34(2) 44 – 46 ,(1972); and N. P. Rudyuk: Nekotorye Vopr. Patol. Beremennosti i Rodov, Vinnitsk. Med. Inst. Vinnitsa 1960 No. 2 251 – 258 (Pub. 1961)] There has been no report on the isolation or prepareation of human placental hyaluronidase so far.

The inventors succeeded in isolation and preparation of hyaluronidase from human placenta in good yield, and found that the preparation thus obtained showed no ill-effect when being parentally administered to test animals and human bodies.

Thus, an object of the present invention is to provide a preparation of human placenta hyaluronidase which has no ill-effect to human body due to the lack of heterogeneous protein.

Another object of the present invention is to provide a method of preparing a hyaluronidase preparation from a readily available source.

According to the present invention, there is provided a process for preparing a hyaluronidase preparation comprising subjecting a human placental tissue to extraction with an aqueous alkaline solution at pH of about 7.5 to about 10.5, harvesting glubulin fraction from the extract, contacting the globulin fraction with an anion exchanger equilibrated with about 0.005 M to about 0.01 M buffer at pH of about 6.0 to about 8.5 and eluting hyaluronidase adsorbed with a buffer of increased molarity and/or lowered pH, and subjecting thus obtained hyaluronidase fraction to gel-filtration.

Now, the present invention will be explained in detail.

Human placental tissue used in the present invention is fresh or frozen one, and is used with or without washing to remove blood. The tissue is minced by an appropriate chopper such as a meat chopper, and homogenized with an aqueous alkaline solution at pH 7.5 – 10.5. All treatments are done preferably at the temperature below 5° C. Unsolubilized material is removed by filtration or centrifugation and the clear extract is obtained. By this alkaline extraction process, the maximum yield of hyaluronidase is achieved and this range of pH keeps the enzyme more stable during the extraction than doing in acidic medium.

Alkalis used in the aqueous alkaline solution are ammonium hydroxide, sodium hydroxide, tris(hydroxymethyl)aminomethane, various boric acid salts, and preferably alkaline buffer containing the above alkalis.

A globulin fraction can be harvested from the clear extract by using any conventional fractionation methods, for instance, salting-out fractionation by ammonium sulfate, fractionation by water-soluble alcohols, by zinc acetate, and electrophoretically, and separated from hemoprotein such as hemoglobin and colored protein contained in the extract.

Among the fractionation methods, ammonium sulfate fractionation and alcohol fractionation processes are recommendable, and the former is most preferable. The extract obtained is adjusted to pH about 6.5 to 7.5, and added with solid or concentrated ammonium sulfate under vigorous stirring to give about 40 to 50% saturation to the resulting solution. The precipitate formed is harvested by centrifugation. Thus obtained precipitate or globulin fraction contains almost all amount of hyaluronidase in the starting placenta. On the other hand, large amounts of impurities such as hemoprotein contained in the original tissue are effectively removed; moreover, huge volume of the original extract can be reduced to a small volume as precipitate sludge. This ammonium sulfate precipitation process may conveniently be performed at room temperature, being its action of enzyme stabilizing and bacteriostatic effects due to ammonium sulfate added.

The alcohol fractionation process is also preferably used to separate hyaluronidase from the extract by precipitating fractionation using watersoluble alcohols such as ethanol and isopropanol. In the case of applying ethanol, for instance, a final solvent concentration of about 20 – 25 percent at pH about 6.5 – 8.5 is an appropriate condition.

Although the ethanol fractionation process usually requires rather strict conditions in temperature, pH and ion strength, the yield and purity achieved by this process do not differ so much from those by ammonium sulfate fractionation.

The globulin fraction harvested as the precipitate, is still heavily contaminated with hypotensive factors, blood type substances, hemoprotein and others, and hence it should further be purified. In order to remove such impurities, the fraction is contacted with an anion exchanger so that hyaluronidase in the fraction is adsorbed selectively.

The precipitate is dissolved in a small amount of water, and ammonium sulfate remaining in the solution is removed by dialysis against water, and the dialysate is contacted with an anion exchanger. The selective adsorption of hyaluronidase is carried out by contacting the dialysate with anion exchangers at a pH of about 6.0 to about 8.5 in a buffer of such a decreased molarity as about 0.005 M to about 0.01 M.

Thus, the dialysate is equilibrated with about 0.005 M — about 0.01 M buffer at a pH of about 6.0 to about 8.5, such as phosphate buffer and tris(hydroxymethyl)aminomethane buffer, and passed through an anion exchanger column which has previously been equilibrated with the same buffer. Hyaluronidase in the dialysate is selectively adsorbed by the anion exchanger.

The anion exchangers used in the step are, for example, a polysaccharide gel with basic groups, such as DEAE-Sephadex (diethylaminoethyl dextran supplied by Pharmacia Co.) and DEAE-Cellulose (diethylaminoethyl cellulose supplied by Brown Co.), a styrenedivinylbenzene (DVB) copolymer matrix with basic groups such as Dowex 1 (styrene-DVB copolymer matrix with quaternary ammonium group), or a phenol-formaldehyde resin with basic groups such as Amberlite XE (supplied by Rohm and Haas Co.).

After washing the anion exchanger with the same buffer as used to remove non-adsorbed impurities, hyaluronidase is eluted with the buffer but having an increased molarity, for example, 0.02 M – 0.10 M with same of lower pH, or with the buffer of a lowered pH, for example, 6.5 – 5.0, according to conventional chromatography technique.

The eluted hyaluronidase fraction is gelfiltered through a highly cross-linked polysaccharide gel molecular sieving such as Sephadex G-150 and G-250 (cross-linked dextran supplied by Pharmacia Co., Sweden) and Sepharose 6-B (agarose gel supplied by Pharmacia Co.), or a polyacrylamide gel molecular sieving such as Biogel P-100 or P-150 (a copolymer of acrylamide and methylenebis acrylamide supplied by BIO-RAD Lab. The filtrate is lyophylized into white powder which is the hyaluronidase preparation of the present invention.

While a satisfactory preparation can be obtained according to the above-mentioned process, hyaluronidase preparation having higher activity may be prepared by inserting, before the contacting of anion exchanger, the treatment of the globulin fraction either with a cation exchanger equilibrated with a buffer having a molarity ranging about 0.01 M to 0.05 M at a pH of about 5 to about 7, or with an anion exchanger which may be same as previously mentioned and is equilibrated with a buffer having a molarity ranging about 0.1 M to 0.2 M at a pH of about 6.0 to about 7.0, in order to previously removing the undesirable impurities already mentioned, as selective adsorptives.

The cation exchanger used is, for example, polysaccharide gel type such as CM-Cellulose (carboxymethylated cellulose supplied by Brown Co.) and CM-Sephadex (carboxymethylated dextran sold by Pharmacia Co.), or methacrylic acid-divinylbenzene copolymer such as Amberlite IRC-50 (supplied by Rohm & Haas Co.), and the actual technique of the treatment is conventional in the art.

In both treatments, the buffer which passed through each of the ion exchangers and containing further purified hyaluronidase is contacted with the anion exchanger under the condition previously mentioned to obtain further purified hyaluronidase fraction which is subjected to gel-filtration.

Alternatively, the impurities contained in the globulin fraction may also be removed by the use of less cross-linked molecular siervings and non-specific adsorbents for facilitating the essential steps, that is, the contacting with the anion exchanger and gelfiltration. For the purpose, the globulin fraction is passed through a molecular sieving such as Sephadex G-100 or G-150 and fractionated into three fractions, that is, higher molecular weight one, a desired fraction of a molecular weight of 50,000 – 100,000 and lower molecular weight fraction. The desired fraction may be contacted with non-specific adsorbents such as charcoal, kaolin and hydroxyapatite, etc. The partially purified fraction thus obtained may be treated with the cation exchanger or anion exchanger according to the procedure in the previous paragraph followed by the essential treatment with the anion exchanger and gel-filtration.

The hyaluronidase preparation of the present invention has no adverse effects when being injected into human bodies. The properties of the human placental hyaluronidase prepared by the present method are as follows: Molecular weight is about 70,000 with isoelectiric point pH 5.2, and its optimal pH ranging 3.6 – 4.0 determined with hyaluronic acid from human umbilical cord as a substrate. The enzyme is very stable when being kept below 30° C at a pH of 6 – 7 in an aqueous solution. On the other hand, it has been reported that the molecular weight, isoelectric point, and the optimal pH of bovine testicular hyaluronidase are 11,000, pH 5.7 and 4.0 – 5.5, respectively.

Comparing with the above parameters of both, human placental hyaluronidase apparently differs from the bovine testicular one.

The present invention will be explained in more detail by following Examples which should not be construed to limit the invention.

In the Examples the assay of hyaluronidase activity is performed by a modification of the methods of Aronson et al. [N. N. Aronson, Jr., E. A. Dadidson J. Biol. Chem. 242(3) 437 – 440 (1967)] and Patel et al. [V. Patel, A. L. Tappel, J. S. O'Brien Biochem. Med. 3 447 – 457 (1972)]. In a test tube, 0.04 M acetate buffer (pH 3.6), 0.15 M NaCl, 150 mcg sodium hyaluronate as a substrate, and enzyme solution are mixed to make a total volume of 0.40 ml, and the reaction mixture is incubated at 37° C for 60 min. After incubation, 50 μl of 50% trichloroacetic acid solution is added to the reaction mixture for stopping the enzymic reaction. To another test tube, as a control, incubation is carried out without addition of enzyme and after the incubation under the same condition to the main experiment, trichloroacetic acid and the enzyme extract are added in this order. No breakdown of hyaluronate is shown in the absence of the enzyme. The acidified reaction mixture by trichloroacetic acid is neutralized with 50 μl of alkali solution of appropriate concentration, usually 3.4 N NaOH is used. The amount of N-acetylhexosamine end group revealed from substrate by the enzymic reaction is determined by the method of Resissig, Strominger and Leloir (J. Biol. Chem. vol. 217, pages 959 – 966, 1955), with using N-acetylglucosamine as a standard. One unit of activity of hyaluronidase is defined as the amount of enzyme that can release 1 μ mole of N-acetylglucosamine residue from hyaluronate added at 37° C per minute.

EXAMPLE [I]

Human frozen placenta, weighed 2676 grams in wet state, was minced by a meat chopper and rinsed three times by suspension and filtration with 10 l of cold physiological saline solution to remove contaminated blood thoroughly. The washed placental tissue obtained weighed 2071 g, and then homogenized by a VirTis 45 homogenizer (sold by The Virtis Co., U.S.A.) with 2.5 times volume of chilled 0.02 M Tris-HCl buffer (pH 9.0) at the top speed of the cutter for 30 seconds. The resulted homogenate, 5,450 ml in total volume, was allowed to stand for 2 hours and centrifuged at 9,600 × g for 15 min. A clear supernatant of 3,950 ml was obtained. The supernatant was adjusted to pH 7.0 by addition of 5 N HCl under vigorous mechanical stirring, followed by addition of 1,290 g solid ammonium sulfate at 0° – 5° C to give approximately 50 percent saturation. The pH of the solution was checked and again adjusted to 7.0 with N sodium hydroxide solution, and allowed to stand for overnight at 0° – 5° C to precipitate completely. The precipitated material was harvested by centrifugation at 9,600 × g for 15 min. and redissolved in 200 ml of water. The solution was then dialyzed against water by a Hollow Fiber Dialyzer Concentrator Model DC-2 (Amicon Corp., U.S.A.) until no sulfate ion was detected. The dialysate was equilibrated with 0.01 M phosphate buffer (pH 8.2) and applied to a DEAE-Cellulose column (4.5 × 50 cm), which had previously equilibrated with the same buffer. The column was washed with the same buffer to remove non-absorbable contaminants. The enzyme was eluated with 0.05 M phosphate buffer (pH 7.5) and the eluated solution, 725 ml in total volume, was desalted by dialysis against water.

The specific activity of the enzyme itself was 4.5 milli units per mg of protein. The degrees of purification at the process of ammonium sulfate fractionation and DEAE-Cellulose column chromatography are calculated as 1.8 fold and 10 fold, respectively.

The hyaluronidase fraction free from the buffer salt was lyophilized in order to concentrate and dissolved in 0.01 M Tris buffer (pH 7.0), and then subjected to ascending gel filtration using Sephadex G-200. The effluent was fractionated and each 2 ml portion was collected in the test tube. Hyaluronidase fraction was pooled and desalted by dialysis against water. After being lyophilized, 20.8 mg of highly purified human placental hyaluronidase was obtained and the specific activity was 17.2 milli units per mg of protein. The degree of purification by the use of Sephadex G-200 is calculated as 3.8 fold.

The hyaluronidase in the preparation had a molecular weight of about 69,000 as determined by gel filtration technique and an isoelectric point of 5.19. The preparation was stable at pH 6.5 at 30° C for at least 24 hours in aqueous solution, but during incubation at 60° C for 30 minutes, 90 percent of the original activity was lost at the same pH. On the other hand, the preparation showed no loss of activity in the repeated treatment of freezing and thawing at least five times, and also stable under the incubation in an aqueous solution at pH 4 – 7.6 at 0° C.

EXAMPLE [II]

One and a half kilogram of the washed placental tissue prepared as in Example I, was homogenized by a waring blender with 2.5 times volume of water. The resulted homogenate was adjusted to pH 9.5 with 2 N sodium hydroxide solution under vigorous stirring and allowed to stand for 1 hour. The extract was filtered through a sheet of cloth under reduced pressure, and the pH of the filtrate was again adjusted to pH 7.0 with 2N hydrochloric acid. To the solution, solid ammonium sulfate was added to give approximately 45 percent saturation, and the resulted precipitate, after standing several hours, was collected by centrifugation at 6,800 × g for 20 minutes. The precipitate was dissolved in a small amount of water, followed by dialysis against water to remove ammonium sulfate. The dialysate was then equilibrated with 0.01 M phosphate buffer (pH 6.0) for the subsequent application onto a CM-Sephadex (C-50) column (3 × 80 cm), which had been equilibrated with the same buffer that was used as eluting solution. Then, the eluate that passed through the column was collected.

A large portion of non active globulin-like protein remained on the CM-Sephadex column in this method, and as the result, hyaluronidase in the eluate was partially purified. The non-absorbed fraction was equilibrated with 0.01 M Tris buffer (pH 8.0) and applied onto a DEAE-Sephadex (A-50) column (2 × 15 cm), which was previously equilibrated with the same buffer. Approximately 30 mg of partially purified human placental hyaluronidase was obtained by lyophilization from the eluate with 0.05 M Tris buffer (pH 7.0), and its specific activity was 11.2 milli units per mg of protein. The degrees of purification by the use of CM-Sephadex and DEAE-Sephadex were 3.5 fold and 8.5 fold, respectively.

Thirty milligrams of the obtained enzyme preparation was dissolved in 2 ml of 0.15 M phosphate buffer (pH 6.5) and then subjected to ascending gel filtration using Sephadex G-200. The effluent was fractionated into each 2 ml portion. Hyaluronidase fractions detected by enzyme assay were pooled and desalted by dialysis against water. After being lyophilized, 15.1 mg of highly purified human placental hyaluronidase was obtained and the specific activity was 19.8 milli units per mg of protein.

The hyaluronidase in the preparation had a molecular weight of about 72,000, an isoelectric point of 5.21. The behaviors in the stability tests are same as those of the preparation obtained in Example I.

What is claimed is:

1. A human placental hyaluronidase preparation free from hypotensive factors, blood type substances, and hemoprotein, said human placental hyaluronidase having a molecular weight of about 70,000, an isoelectric point of pH about 5.2 and enzymatic optimum pH ranging from 3.6 to 4.0, and being stable for at least 24 hours when kept below 30° C. at pH 6–7 in an aqueous solution.

2. A human placental hyaluronidase preparation according to claim 1, wherein the human placental hyaluronidase contained is in the form of lyophilized powder.

3. A process for preparing a hyaluronidase preparation comprising subjecting a human placental tissue to extraction with an aqueous alkaline solution at a pH of about 7.5 to about 10.5, harvesting globulin fraction from the extract, contacting the globulin fraction with an anion exchanger equilibrated with about 0.005 M to about 0.01 M buffer at a pH of about 6.0 to about 8.5 and eluting hyaluronidase adsorbed with a buffer having an increased molarity and/or a lowered pH, and subjecting thus obtained hyaluronidase fraction to gel-filtration.

4. The process for preparing a hyaluronidase preparation according to claim 3, wherein before being contacted with the anion exchanger the globulin fraction is contacted with a cation exchanger equilibrated with about 0.01 M to about 0.05 M buffer at a pH of about 5 to about 7 to pass through a partially purified hyaluronidase fraction which is to be contacted with the anion exchanger.

5. The process for preparing a hyaluronidase preparation according to claim 3, wherein before being contacted with the anion exchanger the globulin fraction is contacted with an anion exchanger equilibrated with about 0.1 M to about 0.2 M buffer at a pH of about 6.0 to about 7.0 to pass through a partially purified hyaluronidase which is to be contacted with the anion exchanger.

6. The process for preparing a hyaluronidase preparation according to claim 3, wherein the harvesting of the globulin fraction is effected by salting out fractionation with ammonium sulfate and collecting a precipitate of up to 40 to 55% saturation at a pH of about 6.5 to about 7.5.

7. The process for preparing a hyaluronidase preparation according to claim 3, wherein the harvesting of the globulin fraction is effected by precipitation with a water-soluble alcohol and collecting a precipitate of up to 20 to 25% saturation at a pH of about 6.5 to 8.5.

8. The process for preparing a hyaluronidase preparation according to claim 3, wherein the whole procedures are effected at a temperature of below 5°C in wet state.

9. The process for preparing a hyaluronidase preparation according to claim 3, wherein the anion exchanger is a polysaccharide gel with basic groups, a styrene-divinylbenzene copolymer gel with basic groups or a phenol formaldehyde resin with basic groups.

10. The process for preparing a hyaluronidase preparation according to claim 3, wherein the anion exchanger is a diethylaminoethyl dextran gel (DEAE-Sephadex), a diethylaminoethyl cellulose (DEAE-Cellulose), a quaternary ammonium-styrene DVB matrix (Dowex 1), or a phenol formaldehyde polyamine resin (Amberlite XE).

11. The process for preparing a hyaluronidase preparation according to claim 3, wherein the gelfiltration is effected by passing the hyaluronidase fraction through a highly cross-linked polysaccharide gel molecular sieving such as Sephadex G-150 and Sephadex G-200, a polyacrylamide gel molecular sieving such as Biogel P-30, or an agarose gel molecular sieving such as Sepharose 6-B.

12. The process for preparing a hyaluronidase preparation according to claim 4, wherein the cation exchanger is a carboxymethyl-cellulose (CM-Cellulose), carboxymethyl dextran (CM-Sephadex), or a carboxylic methacrylic acid-divinylbenzene copolymer (Amberlite IRC-50).

13. The process for preparing a hyaluronidase preparation according to claim 5, wherein the anion exchanger is same as the anion exchanger in claim 1.

14. A hyaluronidase preparation prepared by the process according to claim 3.

* * * * *